United States Patent [19]

Gottschlich et al.

[11] Patent Number: 5,602,144
[45] Date of Patent: Feb. 11, 1997

[54] THIENOPYRIDONES

[75] Inventors: Rudolf Gottschlich, Reinheim; Joachim Leibrock, Griesheim; Christian Noe, Frankfurt, all of Germany; Michael Berger, Vienna, Austria; Hans-Peter Buchstaller, Sulzbach/Ts., Germany

[73] Assignee: Merck Patent Gesellschaft mit Beschrankter Haftung, Darmstadt, Germany

[21] Appl. No.: 572,750

[22] Filed: Dec. 14, 1995

[30] Foreign Application Priority Data

Dec. 15, 1994 [DE] Germany .................. 44 44 815.5

[51] Int. Cl.[6] ............... A61K 31/435; C07D 495/04
[52] U.S. Cl. ........................ 514/301; 546/114
[58] Field of Search ................. 546/114; 514/301

[56] References Cited

U.S. PATENT DOCUMENTS

| | | | |
|---|---|---|---|
| 5,026,700 | 6/1991 | Harrison et al. | 514/233.8 |
| 5,112,821 | 5/1992 | Harrison et al. | 514/301 |
| 5,129,864 | 6/1993 | Suzuki et al. | 514/301 |
| 5,155,115 | 10/1992 | Suzuki et al. | 514/301 |
| 5,348,962 | 9/1994 | Kulagowski et al. | 514/312 |
| 5,378,679 | 1/1995 | Nuebling et al. | 504/246 |

FOREIGN PATENT DOCUMENTS

| | | |
|---|---|---|
| 3982831 | 11/1990 | European Pat. Off. . |
| 481676 | 4/1992 | European Pat. Off. . |
| 503844 | 9/1992 | European Pat. Off. . |
| 505058 | 9/1992 | European Pat. Off. . |

OTHER PUBLICATIONS

Patent Abstracts of Japan, vol. 17, No. 512: JP 5134373 (1993).
Barker et al. J. Chem. Res. No. 7, 1985, pp. 2501–2523.
McQuaid et al., J. Med. Chem., 1992, vol. 35, No. 18, pp. 3423–3425.
Kulagowski et al., "Communications to the Editor":, J. Med. Chem. vol. 37 pp. 1402–1405, 1994.
Leeson et al., "The Glycine Site on the NMDA Receptor . . . ", J. Med. Chem. vol. 27, No. 24, pp. 4053–4067 (1994).

*Primary Examiner*—Bernard Dentz
*Attorney, Agent, or Firm*—Millen, White, Zelano, & Branigan, P.C.

[57] ABSTRACT

Thienopyridone derivatives of the formula I

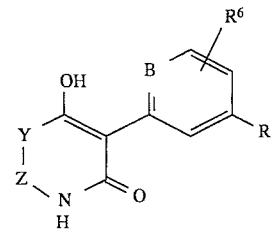

in which
B is CH or N,

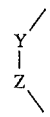

is

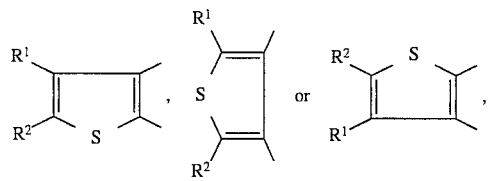

R is H,

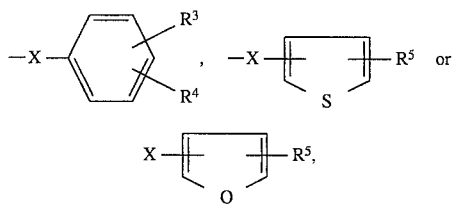

$R^1$, $R^2$ and $R^5$ are in each case H, A or Hal,
$R^3$ and $R^4$ are in each case H, A, OH, OA, Hal, $CF_3$, $NO_2$, $NH_2$, NHA, $N(A)_2$ or NHAc,
$R^6$ is H or Hal,
X is —$CH_2$—, —CO—, —O—, —NH—, —NA— or —S—,
A bis alkyl having 1–4 carbon atoms,
Ac is alkanoyl having 1–6 carbon atoms, or benzoyl and
Hal is F, Cl, Br or I,
and their salts, exhibit a high affinity for binding sites of amino acid receptors and are therefore suitable for treating neurodegenerative diseases.

9 Claims, No Drawings

THIENOPYRIDONES

SUMMARY OF THE INVENTION

The invention relates to novel thienopyridone derivatives of the formula I

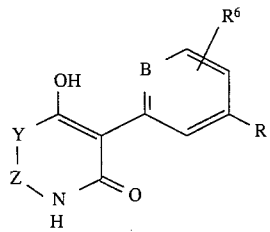

in which

B is CH or N,

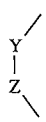

is

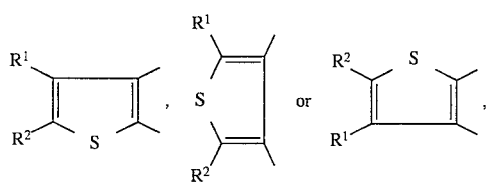

R is H,

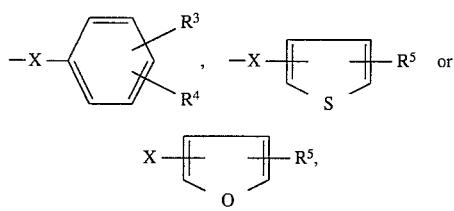

$R^1$, $R^2$ and $R^5$ are in each case H, A or Hal, $R^3$ and $R^4$ are in each case H, A, OH, OA, Hal, $CF_3$, $NO_2$, $NH_2$, NHA, $NA)_2$ or NHAc, $R^6$ is H or Hal, X is —$CH_2$—, —CO—, —O—, —NH—, —NA— or —S—, A is alkyl having 1–4 carbon atoms, Ac is alkanoyl having 1–6 carbon atoms, or benzoyl and Hal is F, Cl, Br or I, and their salts.

Similar compounds have been disclosed by Journal of Medicinal Chemistry 1994, 37, 1402–1405

The underlying object of the invention was to discover novel compounds having valuable properties, in particular those which can be used to prepare medicaments.

It has been found that the compounds of the formula I, and their physiologically harmless i.e., acceptable) salts, possess valuable pharmacological properties. They exhibit a high affinity for binding sites of amino acid receptors, in particular for the glycine, polyamine and/or NMDA (glutamate) binding site of the NMDA receptor (NMDA=N-methyl-D-aspartate). The compounds are suitable, therefore for treating neurodegenerative diseases, including cerebrovascular diseases. The novel active compounds may also be used as analgesics or anxiolytics as well as for treating epilepsy, schizophrenia, Alzheimer's, Parkinson's or Huntington's diseases, cerebral ischaemias or infarctions. In addition, they are suitable for treating psychoses which are due to excessively high amino acid levels.

The [$^3$H]-CGP-39653-binding test for the glutamate binding site of the NMDA receptor can, for example, be carried out using the method of M. A. Stills et al., which is described in Eur. J. Pharmacol. 192, 19–24 (1991). The test for the glycine binding site of the NMDA receptor can be carried out using the method of M. B. Baron et al., which is described in Eur. J. Pharmacol. 206, 149–154 1991). The in-vitro liberation of amino acid can be detected using the method of D. Lobher and P. Lipton Neurosci. Lett. 117, 169–174 (1990)).

The effect against Parkinson's disease, i.e. potentiation of the L-DOPA-induced contralateral rotation in hemiparkinsonian rats, can be detected using the method of U. Ungerstedt and G. W. Arbuthnott, Brain Res 24, 485 1970).

The compounds are particularly suitable for the treatment or prophylaxis of strokes, and for protection against, and for treatment of, cerebral edemas and states of supply deficiency in the central nervous system, in particular hypoxia or anoxia.

The said effects may also be detected or examined using the methods described in the following literature references:

J. W. McDonald, F. S. Silverstein and M. v. Johnston, Eur. J. Pharmacol. 140, 359 (1987); R. Gill, A. C. Foster and G. N. Woodruff, J. Neurosci. 7, 3343 (1987);

S. M. Rottumann, J. H. Thurston, R. E. Hauhart, G. D. Clark and J. S. Soloman, Neurosci. 21, 73 (1987) or M. P. Goldbert, P.-C. Pham and D. W. Choi, Neurosci. Lett. 80, 11 (1987).

The compounds can, therefore, be used as medicinal active compounds in human and veterinary medicine. In addition, they are suitable as intermediates for preparing other compounds possessing valuable properties.

The invention relates to the compounds of the formula I and their salts, and also to a process for preparing these compounds, and their salts, characterized in that a compound of the formula II

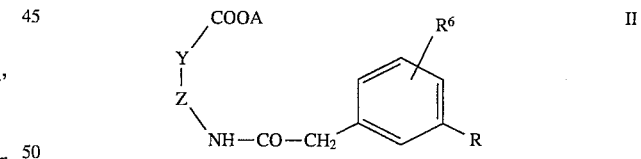

in which

A, B, R, $R^6$ and —Y—Z— have the abovementioned meanings, is treated with a cyclizing agent, and in that, where appropriate, a radical R in a compound of the formula I is transformed into another radical R, and/or a compound of the formula I is converted into one of its salts by being treated with an acid or base.

Unless expressly indicated otherwise, the radicals and/or parameters B, R, $R^1$ to $R^5$, X, —Y—Z—, A, Ac and Hal have, both above and below, the meanings indicated in association with the formula I.

In the abovementioned formulae, A is preferably methyl, ethyl, propyl, isopropyl, and, furthermore, buyl, isobutyl, sec-butyl or tert-butyl.

Ac is preferably formyl, acetyl, propionyl or benzoyl, and, in addition, for example, butyryl, isobutyryl, pentanoyl or hexanoyl.

Hal is preferably fluorine or chlorine, and, in addition, also bromine or iodine.

The radical X is preferably —CH$_2$—, —CO—, —O—, —NH—, and, furthermore, —NA— or —S—.

B is preferably CH, but also N.

The group —Y—Z— is preferably 4-R$^1$-5—R$^2$-thiophen-2,3-diyl, and, furthermore, preferably 2—R$^1$-5—R$^2$-thiphen-3,4-diyl or 3-R$^1$-2—R$^2$-thiophen-4,5-diyl.

R is preferably H, and, furthermore, preferably unsubstituted or monosubstituted phenoxy, specifically and preferably o-, m- or p-methylphenoxy, o-, m- or p-methoxyphenoxy, o-, m- or p-fluorophenoxy, o-, m- or p-chlorophenoxy, and, in addition, preferably o-, m- or p-trifluoromethylphenoxy.

Furthermore, R is preferably unsubstituted or monosubstituted benzyl, specifically and preferably o-, m- or p-methylbenzyl, o-, m- or p-methoxybenzyl, o-, m- or p-fluorobenzyl, o-, m- or p-chlorobenzyl, and, in addition, preferably o-, m- or p-trifluoromethylbenzyl. Furthermore, R is preferably unsubstituted or monosubstituted benzoyl, specifically and preferably o-, m- or p-methylbenzoyl, o-, m- or p-methoxybenzoyl, o -, m- or p-fluorobenzoyl, o -, m- or p-chlorobenzoyl, and, in addition, preferably o-, m- or p-triflouromethyl benzoyl. Furthermore, R is preferably unsubstituted or monosubstituted anilino, specifically and preferably o-, m- or p-methylanilino, o-, m- or p-methoxyanilino, o-, m- or p-fluoroanilino, o-, m- or p-chloroanilino, and, in addition, preferably o-, m- or p-trifluoromethylanilino.

In addition, R is preferably o-, m- or p-nitrophenoxy, o-, m- or p-N,N-dimethylaminophenoxy, o-, m- or p-acetamidophenoxy, o-, m- or p-nitrobenzyl, o-, m- or p-N,N-dimethylaminobenzyl, o-, m- or p-acetamidobenzyl, o-, m- or p-nitrobenzoyl, o-, m- or p-N,N-dimethylaminobenzoyl, o-, m- or p-acetamidobenzoyl, o-, m- or p-nitroanilino, o-, m- or p-N,N-dimethylaminoanilino or o-, m- or p-acetamidoanilino.

R$^1$, R$^2$ and R$^5$ are preferably H, methyl, ethyl, chlorine, and, in addition, propyl or bromine, while R$^3$ and R$^4$ are in each case preferably H, and, in addition, methyl, methoxy, fluorine, chlorine or trifluoromethyl.

R$^6$ is preferably H or F, and, in addition Br.

The compounds of the formula I may possess one or more chiral centers and may, therefore, occur in different-optically active or optically inactive-forms. The formula I encompasses all these forms.

Some preferred groups of compounds can be expressed by the following partial formulae Ia to Ie, which correspond to the formula I and in which the radicals which are not designated in more detail have the meanings indicated in association with formula I, but in which:

in Ia, B is CH;

in Ib, B is N;

in Ic, —Y—Z— is

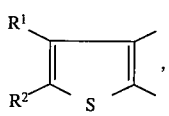

R$^1$ is H or CH$_3$,
R$^2$ is H, CH$_3$, C$_2$H$_5$, Cl or Br,
R$^3$ is H, CH$_3$, OH, OCH$_3$, F, Cl, CF$_3$, NO$_2$, NH$_2$, N(CH$_3$)$_2$ or NHCOCH$_3$,
R$^4$ is H,
R$^5$ is H and
X is —CH$_2$—, —CO—, —O— or —NH—;

in Id, —Y—Z— is

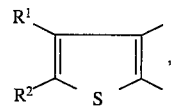

R is H or

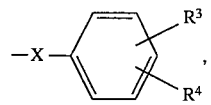

R$^1$ is H or CH$_3$,
R$^2$ is H, CH$_3$, C$_2$H$_5$, Cl or Br,
R$^3$ is H, CH$_3$, OCH$_3$, F, Cl or CF$_3$,
R$^4$ is H, and
X is —CH$_2$—, —CO—, —O— or —NH—;

in Ie, B is CH,
—Y—Z—is

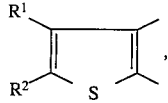

R is H,
R$^1$ is H or CH$_3$, and
R$^2$ is H, CH$_3$, C$_2$H$_5$, Cl or Br.

The compounds of the formula I, and also the starting compounds for their preparation, are otherwise prepared by methods which are known per se, as described in the literature for example in the standard works such as Houben-Weyl, Methoden der organischen Chemie [Methods of organic chemistry], Georg-ThiemeVerlag, Stuttgart; in particular, however, in Journal of Medicinal Chemistry 1994, 37, 1402–1405), and specifically under reaction conditions which are known, and are suitable, for the said reactions. In this context, use can also be made of variants which are known per se but which are not mentioned here in more detail.

If desired, the starting compounds can also be formed in situ, so that they are not isolated from the reaction mixture but are instead immediately subjected to further reaction to form the compounds of the formula I.

The compounds of the formula I can be obtained by treating a compound of the formula II with a cyclizing agent, preferably a base. Examples of bases which may be used are a potassium or sodium alcoholate, such as potassium or sodium methoxide, ethoxide or tert-butoxide, in an inert solvent, preferably the underlying alcohol, NaH in dimethylformamide DMF) or KN[Si(CH$_3$)$_3$]$_2$ in an inert solvent.

The cyclization is expediently carried out at temperatures of between about —100 and about +160° ; it is preferably carried out at between —85 and +50° .

Suitable inert solvents are, in particular, alcohols, such as methanol, ethanol, isopropanol, n-butanol or tert-butanol; ethers, such as diethyl ether, diisopropyl ether, tetrahydrofuran THF) or dioxane; glycol ethers, such as ethylene glycol monomethyl ether or ethylene glycol monoethyl ether methyl glycol or ethyl glycol) or ethylene glycol dimethyl ether (diglyme); ketones, such as acetone or butanone; nitriles, such as acetonitrile; nitro compounds, such as nitromethane or nitrobenzene; carboxylic acids, such as formic acid or acetic acid; esters, such as ethyl acetate; amides, such as DMF, dimethylacetamide or hexamethyl phosphoric triamide EMPT); sulphoxides, such as dimethyl sulphoxide; carbon disulphide; chlorinated hydrocarbons, such as methylene chloride, chloroform, trichloroethylene, 1,2-dichloroethane or carbon tetrachloride; and hydrocarbons, such as hexane, petroleum ether, benzene, toluene or xylene. Mixtures of these solvents with each other are also suitable.

In the compounds of the formula II, A is preferably methyl, and, in addition, ethyl.

As a rule, the starting compounds of the formula II are novel. However, they can be prepared by methods which are known per se. Thus, for example, methyl 2-amino-4-methylthiophene-3-carboxylate can be reacted with, for example, phenylacetyl chloride in an inert solvent, resulting in the formation of methyl 2-phenylacetamido-4-methylthiophene-3-carboxylate. This is expediently carried out at temperatures of between about 0 and about 200° ; the reaction is preferably carried out at between 60° and 90°.

It is furthermore possible to convert a compound of the formula I into another compound of the formula I by converting the radical R into another radical, for example by reducing nitro groups for example by hydrogenating on Raney nickel or Pd/charcoal in an inert solvent such as methanol or ethanol) to form amino groups, and/or functionally modifying free amino and/or hydroxyl groups, and/or liberating functionally modified amino and/or hydroxyl groups by solvolysis or hydrogenolysis.

Thus, free amino groups can, for example, be acylated, in a customary manner, with an acid chloride or acid anhydride, or alkylated with an unsubstituted or substituted alkyl halide, expediently in an inert solvent such as dichloromethane or THF, and/or in the presence of a base such as triethylamine or pyridine, at temperatures of between −60 and +30° . Free hydroxyl groups can be alkylated in an analogous manner.

If desired, a functionally modified amino and/or hydroxyl group in a compound of the formula I can be liberated by solvolysis or hydrogenolysis using customary methods. Thus, a compound of the formula I which contains an NHCOA or an OA group can, for example, be converted into the corresponding compound of the formula I which contains an $NH_2$ or an OH group instead.

Acylated amines of the formula I in which the phenyl radical or pyridyl radical is substituted once by NHCOalkyl can be cleaved, resulting in the formation of the corresponding amino derivatives. For example, the acylamino compounds can be cleaved by treating them with methanolic potassium hydroxide solution at about 20°–140°.

Ethers of the formula I in which the phenyl radical or pyridyl radical is substituted once by O-alkyl can be cleaved, resulting in the formation of the corresponding hydroxyl derivatives. For example, the ethers can be cleaved by treating them with dimethyl sulphide/boron tribromide complex, for example in toluene, ethers such as THF, or dimethyl sulphoxide, or by fusing them with pyridine hydrohalides or aniline hydrohalides, preferably pyridine hydrochloride, at about 150°–250° , or by treating them with diisobutylaluminium hydride in toluene at about 0°–110°.

A base of the formula I can be converted with an acid into the affiliated acid addition salt, for example by reacting equivalent quantities of the base and of the acid in an inert solvent such as ethanol, and then evaporating. Acids which yield physiologically harmless salts are particularly suitable for this reaction. Thus, inorganic acids can be used, for example sulphuric acid, nitric acid, hydrohalic acids, such as hydrochloric acid -or hydrobromic acid, phosphoric acids, such as orthophosphoric acid, and sulphamic acid, and, in addition, organic acids, in particular aliphatic, alicyclic, araliphatic, aromatic or heterocyclic monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalenemonosulphonic acid, naphthalenedisulphonic acid and laurylsulphuric acid. Salts with physiologically harmful acids, for example picrates, can be used to isolate and/or purify the compounds of the formula I.

On the other hand, compounds of the formula I can be converted with bases for example sodium hydroxide or potassium hydroxide or sodium carbonate or potassium carbonate) into the corresponding metal salts, in particular alkali metal salts or alkaline earth metal salts, or into the corresponding ammonium salts.

The invention also relates to the use of the compounds of the formula I, and their physiologically harmless salts, for producing pharmaceutical preparations, in particular by a non-chemical route. In this context, they can be brought into a suitable dosage form together with at least one solid, liquid and/or semiliquid carrier or auxiliary substance and, where appropriate, in combination with one or more additional active compounds.

The invention furthermore relates to pharmaceutical preparations which contain at least one compound of the formula I and/or one of its physiologically harmless salts.

These preparations can be used as medicaments in human or veterinary medicine. Suitable carrier substances are organic or inorganic substances which are suitable for enteral for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc or vaseline. Tablets, pills, coated tablets, capsules, powders, granules, syrups, juices or drops serve, in particular, for oral use, suppositories serve for rectal use, solutions, preferably oily or aqueous solutions, and, in addition, suspensions, emulsions or implants, serve for parenteral use, while ointments, creams or powders serve for topical use. The novel compounds can also be lyophilized, and the resulting lyophilizates can be used, for example for preparing injection preparations. The listed preparations can be sterilized and/or contain auxiliary substances such as lubricants, preservatives, stabilizers and/or wetting agents, emulsifiers, salts for influencing the osmotic pressure, buffer substances, dyes, flavourings and/or aromatizing agents. If desired, they can also contain one or more additional active compounds, for example one or more vitamins.

The compounds of the formula I, and their physiologically harmless salts, can be used in the control of diseases, in particular conditions of pain, but also for reducing the secondary damage following an ischaemia. The compounds are particularly suitable for treating neurodegenerative diseases and diseases which are caused by a malfunction at the glycine, polyamine or glutamate binding site of the NMDA receptor.

In this context, the novel substances are, as a rule, preferably administered in doses of between about 1 and 500 mg, in particular of between 5 and 100 per dosage unit. The daily dose is preferably between about 0.02 and 10 mg/kg of body weight. However, the specific dose for each particular patient depends on a wide variety of factors, for example on the activity of the specific compound employed, on the age, body weight, general state of health and sex, on the nutrition, on the time and route of administration, on the speed of excretion, on the drug combination and on the severity of the particular disease to which the therapy applies. Oral administration is preferred.

In the following examples, "customary working-up" denotes: if necessary, water is added, if necessary, depending on the constitution of the end product, the pH of the mixture is adjusted to pH values of between 2 and 10, and the mixture is then extracted with ethyl acetate or dichloromethane; the organic phase is then separated off, dried over sodium sulphate and evaporated, and the residue is purified by chromatography on silica gel and/or by crystallization. Rf values on silica gel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. P 44 44 815.5, filed Dec. 15, 1994, are hereby incorporated by reference.

EXAMPLE 1

A solution of 0.6 g of methyl 5-chloro-4-methyl-2-phenylacetamido) thiophene-3-carboxylate (m.p. 105°–107°; obtainable by chlorinating the corresponding chlorine-free compound with N- chlorosuccinimide) in 20 ml of THF is cooled down to −70° . 8.16 ml of a 0.5 molar solution of $KN(Si(CH_3)_3)_2$ in toluene are then added dropwise. The reaction solution is slowly brought to room temperature and then evaporated. The residue is taken up in water, and this solution is extracted several times with diethyl ether. The aqueous phase is then acidified with 2 N HCl, and the precipitate is filtered off, washed with water and, after having been digested with diethyl ether, filtered off once again and dried. 2-Chloro-3-methyl-4-hydroxy-5-phenyl-6,7-dihydrothieno[2,3-b]pyridin-6-one is obtained, Rf $CH_2Cl_2$/MeOH 10:1) 0.43.

EXAMPLES 2 to 8

The following 2-$R^2$-3-$R^1$-4-hydroxy- 5-phenyl-6,7-dihydrothieno [2,3-b]pyridin-6-ones:

| Ex. | $R^1$ | $R^2$ | Rf | ($CH_2Cl_2$/MeOH 10:1) |
|---|---|---|---|---|
| 2 | Me | H | 0.43 | |
| 3 | H | Me | 0.36 | |
| 4 | Me | Me | 0.49 | |
| 5 | H | Et | 0.44 | |
| 6 | H | H | 0.31 | |
| 7 | Me | Br | 0.38 | |
| 8 | H | Br | 0.34 | | are obtained, in analogy with Example 1, from the following methyl or ethyl 2-phenylacetamido-4-$R^1$-5-$R^2$-thiophene-3-carboxylates:

| Ex. | $R^1$ | $R^2$ | A | M.p. |
|---|---|---|---|---|
| 2 | Me | H | Me | 105.5–106.5° |
| 3 | H | Me | Me | 110.5–111.5° |
| 4 | Me | Me | Et | 84–86° |
| 5 | H | Et | Me | 105–106° |
| 6 | H | H | Me | 90–92° (known!) |
| 7 | Me | Br | Me | 105–106.5° |
| 8 | H | Br | Me | — |

EXAMPLES 9 to 72

The following 2-chloro-3-methyl-4-hydroxy-5-3-R-phenyl)-6,7-dihydrothieno [2,3-b]pyridin-6-ones:

| Ex. | R |
|---|---|
| 9 | phenoxy, Rf 0.44 |
| 10 | o-methylphenxoy |
| 11 | m-methylphenoxy |
| 12 | p-methylphenoxy |
| 13 | o-methoxyphenoxy |
| 14 | m-methoxyphenoxy |
| 15 | p-methoxyphenoxy |
| 16 | o-fluorophenoxy |
| 17 | m-fluorophenoxy |
| 18 | p-fluorophenoxy |
| 19 | o-chlorophenoxy |
| 20 | m-chlorophenoxy |
| 21 | p-chlorophenoxy |
| 22 | o-trifluoromethylphenoxy |
| 23 | m-trifluoromethylphenoxy |
| 24 | p-trifluoromethylphenoxy |
| 25 | benzyl |
| 26 | o-methylbenzyl |
| 27 | m-methylbenzyl |
| 28 | p-methylbenzyl |
| 29 | o-methoxybenzyl |
| 30 | m-methoxybenzyl |
| 31 | p-methoxybenzyl |
| 32 | o-fluorobenzyl |
| 33 | m-fluorobenzyl |
| 34 | p-fluorobenzyl |
| 35 | o-chlorobenzyl |
| 36 | m-chlorobenzyl |
| 37 | p-chlorobenzyl |
| 38 | o-trifluoromethylbenzyl |
| 39 | m-trifluoromethylbenzyl |
| 40 | p-trifluoromethylbenzyl |
| 41 | benzoyl |
| 42 | o-methylbenzoyl |
| 43 | m-methylbenzoyl |
| 44 | p-methylbenzoyl |
| 45 | o-methoxybenzoyl |
| 46 | m-methoxybenzoyl |
| 47 | p-methoxybenzoyl |
| 48 | o-fluorobenzoyl |
| 49 | m-fluorobenzoyl |
| 50 | p-fluorobenzoyl |
| 51 | o-trifluoromethylbenzoyl |
| 52 | m-trifluoromethylbenzoyl |
| 53 | p-trifluoromethylbenzoyl |
| 54 | o-chlorobenzoyl |
| 55 | m-chlorobenzoyl |
| 56 | p-chlorobenzoyl |
| 57 | anilino |
| 58 | o-methylanilino |
| 59 | m-methylanilino |
| 60 | p-methylanilino |
| 61 | o-methoxyanilino |
| 62 | m-methoxyanilino |
| 63 | p-methoxyanilino |
| 64 | o-fluoroanilino |
| 65 | m-fluoroanilino |
| 66 | p-fluoroanilino |
| 67 | o-chloroanilino |

-continued

| Ex. | R |
|---|---|
| 68 | m-chloroanilino |
| 69 | p-chloroanilino |
| 70 | o-trifluoromethylanilino |
| 71 | m-trifluoromethylanilino |
| 72 | p-trifluoromethylanilino | are obtained, in analogy with Example 1, from the following methyl 2-(3-R-phenyl)acetamido-4-methyl-5-chlorothiophene-3-carboxylates:

| Ex. | R |
|---|---|
| 9 | phenoxy, m.p. 113–115° |
| 10 | o-methylphenoxy |
| 11 | m-methylphenoxy |
| 12 | p-methylphenoxy |
| 13 | o-methoxyphenoxy |
| 14 | m-methoxyphenoxy |
| 15 | p-methoxyphenoxy |
| 16 | o-fluorophenoxy |
| 17 | m-fluorophenoxy |
| 18 | p-fluorophenoxy |
| 19 | o-chlorophenoxy |
| 20 | m-chlorophenoxy |
| 21 | p-chlorophenoxy |
| 22 | o-trifluoromethylphenoxy |
| 23 | m-trifluoromethylphenoxy |
| 24 | p-trifluoromethylphenoxy |
| 25 | benzyl |
| 26 | o-methylbenzyl |
| 27 | m-methylbenzyl |
| 28 | p-methylbenzyl |
| 29 | o-methoxybenzyl |
| 30 | m-methoxybenzyl |
| 31 | p-methoxybenzyl |
| 32 | o-fluorobenzyl |
| 33 | m-fluorobenzyl |
| 34 | p-fluorobenzyl |
| 35 | o-chlorobenzyl |
| 36 | m-chlorobenzyl |
| 37 | p-chlorobenzyl |
| 38 | o-trifluoromethylbenzyl |
| 39 | m-trifluoromethylbenzyl |
| 40 | p-trifluoromethylbenzyl |
| 41 | benzoyl |
| 42 | o-methylbenzoyl |
| 43 | m-methylbenzoyl |
| 44 | p-methylbenzoyl |
| 45 | o-methoxybenzoyl |
| 46 | m-methoxybenzoyl |
| 47 | p-methoxybenzoyl |
| 48 | o-fluorobenzoyl |
| 49 | m-fluorobenzoyl |
| 50 | p-fluorobenzoyl |
| 51 | o-trifluoromethylbenzoyl |
| 52 | m-trifluoromethylbenzoyl |
| 53 | p-trifluoromethylbenzoyl |
| 54 | o-chlorobenzoyl |
| 55 | m-chlorobenzoyl |
| 56 | p-chlorobenzoyl |
| 57 | anilino |
| 58 | o-methylanilino |
| 59 | m-methylanilino |
| 60 | p-methylanilino |
| 61 | o-methoxyanilino |
| 62 | m-methoxyanilino |
| 63 | p-methoxyanilino |
| 64 | o-fluoroanilino |
| 65 | m-fluoroanilino |
| 66 | p-fluoroanilino |
| 67 | o-chloroanilino |
| 68 | m-chloroanilino |
| 69 | p-chloroanilino |
| 70 | o-trifluoromethylanilino |

-continued

| Ex. | R |
|---|---|
| 71 | m-trifluoromethylanilino |
| 72 | p-trifluoromethylanilino. |

EXAMPLES 73 to 136

The following 2-chloro-3-methyl-4-hydroxy-5-4-R-2-pyridyl)-6,7-dihydrothieno [2,3-6-ones:

| Ex. | R |
|---|---|
| 73 | phenoxy |
| 74 | o-methylphenoxy |
| 75 | m-methylphenoxy |
| 76 | p-methylphenoxy |
| 77 | o-methoxyphenoxy |
| 78 | m-methoxyphenoxy |
| 79 | p-methoxyphenoxy |
| 80 | o-fluorophenoxy |
| 81 | m-fluorophenoxy |
| 82 | p-fluorophenoxy |
| 83 | o-chlorophenoxy |
| 84 | m-chlorophenoxy |
| 85 | p-chlorophenoxy |
| 86 | o-trifluoromethylphenoxy |
| 87 | m-trifluoromethylphenoxy |
| 88 | p-trifluoromethylphenoxy |
| 89 | benzyl |
| 90 | o-methylbenzyl |
| 91 | m-methylbenzyl |
| 92 | p-methylbenzyl |
| 93 | o-methoxybenzyl |
| 94 | m-methoxybenzyl |
| 95 | p-methoxybenzyl |
| 96 | o-fluorobenzyl |
| 97 | m-fluorobenzyl |
| 98 | p-fluorobenzyl |
| 99 | o-chlorobenzyl |
| 100 | m-chlorobenzyl |
| 101 | p-chlorobenzyl |
| 102 | o-trifluoromethylbenzyl |
| 103 | m-trifluoromethylbenzyl |
| 104 | p-trifluoromethylbenzyl |
| 105 | benzoyl |
| 106 | o-methylbenzoyl |
| 107 | m-methylbenzoyl |
| 108 | p-methylbenzoyl |
| 109 | o-methoxybenzoyl |
| 110 | m-methoxybenzoyl |
| 111 | p-methoxybenzoyl |
| 112 | o-fluorobenzoyl |
| 113 | m-fluorobenzoyl |
| 114 | p-fluorobenzoyl |
| 115 | o-trifluoromethylbenzoyl |
| 116 | m-trifluoromethylbenzoyl |
| 117 | p-trifluoromethylbenzoyl |
| 118 | o-chlorobenzoyl |
| 119 | m-chlorobenzoyl |
| 120 | p-chlorobenzoyl |
| 121 | anilino |
| 122 | o-methylanilino |
| 123 | m-methylanilino |
| 124 | p-methylanilino |
| 125 | o-methoxyanilino |
| 126 | m-methoxyanilino |
| 127 | p-methoxyanilino |
| 128 | o-fluoroanilino |
| 129 | m-fluoroanilino |
| 130 | p-fluoroanilino |
| 131 | o-chloroanilino |
| 132 | m-chloroanilino |
| 133 | p-chloroanilino |
| 134 | o-trifluoromethylanilino |
| 135 | m-trifluoromethylanilino |
| 136 | p-trifluoromethylanilino | are obtained, in analogy with Example 1, from the following methyl 2-(4-R-2-pyridyl)acetamido-4-methyl-5-chlorothiophene-3-carboxylates:

| Ex. | R |
|---|---|
| 73 | phenoxy |
| 74 | o-methylphenoxy |
| 75 | m-methylphenoxy |
| 76 | p-methylphenoxy |
| 77 | o-methoxyphenoxy |
| 78 | m-methoxyphenoxy |
| 79 | p-methoxyphenoxy |
| 80 | o-fluorophenoxy |
| 81 | m-fluorophenoxy |
| 82 | p-fluorophenoxy |
| 83 | o-chlorophenoxy |
| 84 | m-chlorophenoxy |
| 85 | p-chlorophenoxy |
| 86 | o-trifluoromethylphenoxy |
| 87 | m-trifluoromethylphenoxy |
| 88 | p-trifluoromethylphenoxy |
| 89 | benzyl |
| 90 | o-methylbenzyl |
| 91 | m-methylbenzyl |
| 92 | p-methylbenzyl |
| 93 | o-methoxybenzyl |
| 94 | m-methoxybenzyl |
| 95 | p-methoxybenzyl |
| 96 | o-fluorobenzyl |
| 97 | m-fluorobenzyl |
| 98 | p-fluorobenzyl |
| 99 | o-chlorobenzyl |
| 100 | m-chlorobenzyl |
| 101 | p-chlorobenzyl |
| 102 | o-trifluoromethylbenzyl |
| 103 | m-trifluoromethylbenzyl |
| 104 | p-trifluoromethylbenzyl |
| 105 | benzoyl |
| 106 | o-methylbenzoyl |
| 107 | m-methylbenzoyl |
| 108 | p-methylbenzoyl |
| 109 | o-methoxybenzoyl |
| 110 | m-methoxybenzoyl |
| 111 | p-methoxybenzoyl |
| 112 | o-fluorobenzoyl |
| 113 | m-fluorobenzoyl |
| 114 | p-fluorobenzoyl |
| 115 | o-trifluoromethylbenzoyl |
| 116 | m-trifluoromethylbenzoyl |
| 117 | p-trifluoromethylbenzoyl |
| 118 | o-chlorobenzoyl |
| 119 | m-chlorobenzoyl |
| 120 | p-chlorobenzoyl |
| 121 | anilino |
| 122 | o-methylanilino |
| 123 | m-methylanilino |
| 124 | p-methylanilino |
| 125 | o-methoxyanilino |
| 126 | m-methoxyanilino |
| 127 | p-methoxyanilino |
| 128 | o-fluoroanilino |
| 129 | m-fluoroanilino |
| 130 | p-fluoroanilino |
| 131 | o-chloroanilino |
| 132 | m-chloroanilino |
| 133 | p-chloroanilino |
| 134 | o-trifluoromethylanilino |
| 135 | m-trifluoromethylanilino |
| 136 | p-trifluoromethylanilino. |

EXAMPLES 137 to 143

The following 2-$R^2$-3-$R^1$-4-hydroxy-5-(2-pyridyl)-6,7-dihydrothieno[2,3-b]pyridin-6-ones:

| Ex. | $R^1$ | $R^2$ |
|---|---|---|
| 137 | Me | H |
| 138 | H | Me |
| 139 | Me | Me |
| 140 | H | Et |
| 141 | H | H |
| 142 | Me | Br |
| 143 | H | Br | are obtained, in analogy with Example 1, from the following methyl 2-2-pyridyl) acetamido-4-$R^1$-5-$R^2$-thiophene-3-carboxylates:

| Ex. | $R^1$ | $R^2$ |
|---|---|---|
| 137 | Me | H |
| 138 | H | Me |
| 139 | Me | Me |
| 140 | H | Et |
| 141 | H | H |
| 142 | Me | Br |
| 143 | H | Br. |

EXAMPLES 144–147

The following 2-chloro-3-methyl-4-hydroxy-5-(3-R-phenyl)-6,7-dihydrothieno[2,3-b]pyridin-6-ones:

| Ex. | R |
|---|---|
| 144 | 2-thienylcarbonyl |
| 145 | 2-thienylmethyl |
| 146 | 3-thienylcarbonyl |
| 147 | 3-thienylmethyl | are obtained, in analogy with Example 1, from the following methyl 2-(3-R-phenyl) acetamido-4-methyl-5-chlorothiophene-3-carboxylates:

| Ex. | R |
|---|---|
| 144 | 2-thienylcarbonyl |
| 145 | 2-thienylmethyl |
| 146 | 3-thienylcarbonyl |
| 147 | 3-thienylmethyl. |

EXAMPLES 148–183

The following 2-chloro-3-methyl-4-hydroxy-5-3-R-phenyl)-6,7-dihydrothieno[2,3-b]pyridin-6-ones:

| Ex. | R |
|---|---|
| 148 | o-nitrophenoxy |
| 149 | m-nitrophenoxy |
| 150 | p-nitrophenoxy |
| 151 | o-N,N-dimethylaminophenoxy |
| 152 | m-N,N-dimethylaminophenoxy |
| 153 | p-N,N-dimethylaminophenoxy |
| 154 | o-acetamidophenoxy |
| 155 | m-acetamidophenoxy |
| 156 | p-acetamidophenoxy |
| 157 | o-nitrobenzyl |
| 158 | m-nitrobenzyl |

-continued

| Ex. | R |
|---|---|
| 159 | p-nitrobenzyl |
| 160 | o-N,N-dimethylaminobenzyl |
| 161 | m-N,N-dimethylaminobenzyl |
| 162 | p-N,N-dimethylaminobenzyl |
| 163 | o-acetamidobenzyl |
| 164 | m-acetamidobenzyl |
| 165 | p-acetamidobenzyl |
| 166 | o-nitrobenzoyl |
| 167 | m-nitrobenzoyl |
| 168 | p-nitrobenzoyl |
| 169 | o-N,N-dimethylaminobenzoyl |
| 170 | m-N,N-dimethylaminobenzoyl |
| 171 | p-N,N-dimethylaminobenzoyl |
| 172 | o-acetamidobenzoyl |
| 173 | m-acetamidobenzoyl |
| 174 | p-acetamidobenzoyl |
| 175 | o-nitroanilino |
| 176 | m-nitroanilino |
| 177 | p-nitroanilino |
| 178 | o-N,N-dimethylaminoanilino |
| 179 | m-N,N-dimethylaminoanilino |
| 180 | p-N,N-dimethylaminoanilino |
| 181 | o-acetamidoanilino |
| 182 | m-acetamidoanilino |
| 183 | p-acetamidoanilino | are obtained, in analogy with Example 1, from the following methyl 2-3-R-phenyl) acetamido-4-methyl- 5-chlorothiophene-3-carboxylates:

| Ex. | R |
|---|---|
| 148 | o-nitrophenoxy |
| 149 | m-nitrophenoxy |
| 150 | p-nitrophenoxy |
| 151 | o-N,N-dimethylaminophenoxy |
| 152 | m-N,N-dimethylaminophenoxy |
| 153 | p-N,N-dimethylaminophenoxy |
| 154 | o-acetamidophenoxy |
| 155 | m-acetamidophenoxy |
| 156 | p-acetamidophenoxy |
| 157 | o-nitrobenzyl |
| 158 | m-nitrobenzyl |
| 159 | p-nitrobenzyl |
| 160 | o-N,N-dimethylaminobenzyl |
| 161 | m-N,N-dimethylaminobenzyl |
| 162 | p-N,N-dimethylaminobenzyl |
| 163 | o-acetamidobenzyl |
| 164 | m-acetamidobenzyl |
| 165 | p-acetamidobenzyl |
| 166 | o-nitrobenzoyl |
| 167 | m-nitrobenzoyl |
| 168 | p-nitrobenzoyl |
| 169 | o-N,N-dimethylaminobenzoyl |
| 170 | m-N,N-dimethylaminobenzoyl |
| 171 | p-N,N-dimethylaminobenzoyl |
| 172 | o-acetamidobenzoyl |
| 173 | m-acetamidobenzoyl |
| 174 | p-acetamidobenzoyl |
| 175 | o-nitroanilino |
| 176 | m-nitroanilino |
| 177 | p-nitroanilino |
| 178 | o-N,N-dimethylaminoanilino |
| 179 | m-N,N-dimethylaminoanilino |
| 180 | p-N,N-dimethylaminoanilino |
| 181 | o-acetamidoanilino |
| 182 | m-acetamidoanilino |
| 183 | p-acetamidoanilino. |

EXAMPLE 184

7-Hydroxy-6-phenyl-4,5-dihydrothieno[3,2-b]-pyridine-5-one, $R_f$ 0.31 (dichloromethane/methanol 10:1), is obtained, in analogy with Example 1, by cyclization, from methyl 3-phenylacetamidothiophene-2-carboxylate.

EXAMPLE 185

The compound 4-hydroxy-3-phenyl-1,2-dihydrothieno[3,4-b]pyridin-2-one, $R_f$ 0.37 dichloromethane/methanol 10:1), is obtained, in analogy with Example 1, from methyl 4-phenylacetamidothiophene-3-carboxylate.

EXAMPLE 186

20 mg of platinum oxide are added to a solution of 4.28 g of 2-chloro-3-methyl-4-hydroxy-5-(3-m-nitro-phenoxyphenyl)-6,7-dihydrothieno[2,3-b]pyridin-6-one in 50 ml of 95% ethanol. Hydrogen is passed through the solution until three molar equivalents have been absorbed. The platinum is filtered off and the alcohol is distilled off. 2-Chloro-3-methyl-4-hydroxy-5-(3-m-aminophenoxyphenyl)-6,7-dihydrothieno[2,3-b]pyridin-6-one is obtained.

EXAMPLE 187

A solution of 4.4 g of 2-chloro-3-methyl-4-hydroxy-5-3-o-acetamidophenoxyphenyl)-6,7-dihydrothieno [2,3-b]pyridin-6-one in 80 ml of 10% methanolic KOH solution is boiled for 48 hours. 2-Chloro-3-methyl-4-hydroxy-5-3-o-aminophenoxyphenyl)-6,7-dihydro-thieno[2,3-b]pyridin-6-one is obtained after the customary working-up.

EXAMPLE 188

A mixture of 4.25 g of 2-chloro-3-methyl-4-hydroxy-5-(3-p-methoxybenzoylphenyl)-6,7-dihydrothieno [2,3-b]pyridin-6-one and 3.5 g of pyridine hydrochloride is stirred at 160° for 3 hours. 2-Chloro-3-methyl-4-hydroxy-5-3-p-hydroxybenzoylphenyl)-6,7-dihydrothieno [2,3-b]pyridin-6-one is obtained after the customary working-up.

EXAMPLES 189–199

The following 2-$R^2$-3-$R^1$-4-hydroxy-5-3-R-4-$R^6$-phenyl)-6,7-dihydrothieno [2,3-b]pyridin- 6-ones:

| Ex. | R | $R^6$ | $R^1$ | $R^2$ | Rf (CH$_2$Cl$_2$/MeOH 10:1) |
|---|---|---|---|---|---|
| 189 | H | F | H | H | 0.34 |
| 190 | H | H | Ethyl | H | 0.38 |
| 191 | H | H | Ethyl | Br | 0.35 |
| 192 | H | H | Ethyl | Cl | 0.4 |
| 193 | OC$_6$H$_5$ | H | Methyl | H | 0.39 |
| 194 | OC$_6$H$_5$ | H | Ethyl | Cl | 0.59 |
| 195 | H | H | CH(CH$_3$)$_2$ | Cl | 0.56 |
| 196 | OC$_6$H$_5$ | H | CH(CH$_3$)$_2$ | Cl | 0.58 |
| 197 | OC$_6$H$_5$ | H | cyclohexyl | Cl | 0.44 |
| 198 | OC$_6$H$_5$ | H | cyclopropyl | Cl | 0.42 |
| 199 | OC$_6$H$_5$ | H | tert.-butyl | Cl | 0.45 | are obtained, in analogy with Example 1, from the following methyl 2-(3-R-4-$R^6$-phenyl)acetamido-4-$R^1$-5-$R^2$-thiophene-3-carboxylates:

| Ex. | R | $R^6$ | $R^1$ | $R^2$ | m.p. |
|---|---|---|---|---|---|
| 189 | H | F | H | H | 102.5–104° |
| 190 | H | H | Ethyl | H | 116–117° |
| 191 | H | H | Ethyl | Br | 92–93° |
| 192 | H | H | Ethyl | Cl | 89.5–91.5 |
| 193 | OC$_6$H$_5$ | H | Methyl | H | 83–85° |
| 194 | OC$_6$H$_5$ | H | Ethyl | Cl | 116–118° |
| 195 | H | H | CH(CH$_3$)$_2$ | Cl | 70–71° |
| 196 | OC$_6$H$_5$ | H | CH(CH$_3$)$_2$ | Cl | 61–63° |
| 197 | OC$_6$H$_5$ | H | cyclohexyl | Cl | 83.5–84.5° |
| 198 | OC$_6$H$_5$ | H | cyclopropyl | Cl | 95–97° |
| 199 | OC$_6$H$_5$ | H | tert.-butyl | Cl | 63.5–66°. |

The following examples relate to pharmaceutical preparations which contain active compounds of the formula I or their salts.

EXAMPLE A

Tablets and coated tablets

Tablets of the following composition, which, as required, are coated with a customary sugar coating surface on a sucrose base, are pressed in the customary manner:

| | |
|---|---|
| active compound of the formula I | 100 mg |
| microcrystalline cellulose | 278.8 mg |
| lactose | 110 mg |
| corn starch | 11 mg |
| magnesium stearate | 5 mg |
| finely divided silicon dioxide | 0.2 mg |

EXAMPLE B

Hard gelatin capsules

Customary two-part hard gelatin capsules are in each case filled with

| | |
|---|---|
| active compound of the formula I | 100 mg |
| lactose | 150 mg |
| cellulose | 50 mg |
| magnesium stearate | 6 mg |

EXAMPLE C

Soft gelatin capsules

Customary soft gelatin capsules are filled with a mixture comprising in each case 50 mg of active compound and 250 mg of olive oil.

EXAMPLE D

Ampoules

A solution of 200 g of active compound in 2 kg of 1,2-propanediol is made up to 10 l with water and used to fill ampoules such that each ampoule contains 20 mg of active compound.

EXAMPLE E

Aqueous suspension for oral administration

An aqueous suspension of the active compound is prepared in the customary manner. The single dose 5 ml) contains 100 mg of active compound, 100 mg of Na carboxymethylcellulose, 5 mg of Na benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:
1. Thienopyridones of the formula I

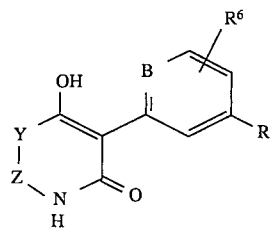

wherein

B is CH or N,

is

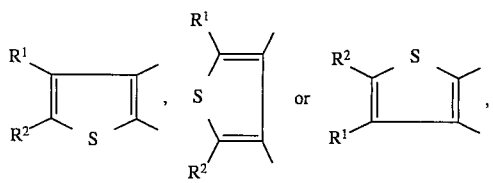

R is H,

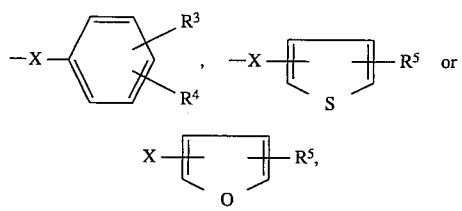

$R^1$, $R^2$ and $R^5$ are in each case H, A or Hal, $R^3$ and $R^4$ are in each case H, A, OH, OA, Hal, $CF_3$, $NO_2$, $NH_2$, NHA, N $(A)_2$ or NHAc, $R^6$ is H or Hal, X is —$CH_2$—, —CO—, —O—, —NH—, —NA— or —S—, A is $C_{1-4}$-alkyl, Ac is $C_{1-6}$-alkanoyl, or benzoyl and Hal is F, Cl, Br or I, or a pharmacologically acceptable salt thereof.

2. A compound according to claim 1, of formula Ia, wherein B is CH.

3. A compound according to claim 1, of formula Ib, wherein B is N.

4. A compound according to claim 1, of formula Ic, wherein —Y—Z— is

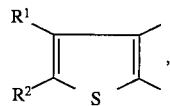

$R^1$ is H or $CH_3$, $R^2$ is H, $CH_3$, $C_2H_5$, Cl or Br,

R³ is H, CH₃, OH, OCH₃, F, Cl, CF₃, NO₂, NH₂, N(CH₃)₂ or NHCOCH₃,
R⁴ is H,
R⁵ is H and
X is —CH₂—, —CO—, —O— or —NH—.

5. A compound according to claim 1, of formula Id, wherein —Y—Z— is

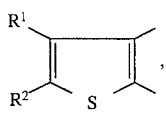

R is H or

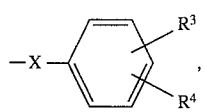

R¹ is H or CH₃,
R² is H, CH₃, C₂H₅, Cl or Br,
R³ is H, CH₃, OCH₃, F, Cl or CF₃,
R⁴ is H, and
X is —CH₂—, —CO—, —O— or —NH—.

6. A compound according to claim 1, of formula Ie, wherein B is CH, —Y—Z— is

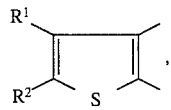

R is H,
R¹ is H or CH₃, and
R² is H, CH₃, C₂H₅, Cl or Br.

7. A pharmaceutical composition comprising a compound according to claim 1 and a pharmaceutically acceptable carrier.

8. A method for the treatment of cerebral ischaemia or schizophrenia, comprising administering a compound of claim 1.

9. 2-Chloro-3-methyl-4-hydroxy-5-phenyl-6,7-dihydrothieno{2,3-b}pyridin-6-one, a compound of claim 1.

* * * * *